United States Patent [19]

Genese et al.

[11] Patent Number: 4,496,348

[45] Date of Patent: Jan. 29, 1985

[54] VENIPUNCTURE DEVICE

[75] Inventors: Joseph N. Genese, Waukegan; Charles H. Seberg, Libertyville, both of Ill.

[73] Assignee: Abbott Laboratories, North Chicago, Ill.

[21] Appl. No.: 98,566

[22] Filed: Nov. 29, 1979

[51] Int. Cl.³ .................. A61M 5/00; A61M 25/00
[52] U.S. Cl. ..................................... 604/167; 604/169
[58] Field of Search ............... 128/214.2, 214.4, 221, 128/348, 349 R, 347, 214 R; 215/247; 604/167, 169

[56] References Cited

U.S. PATENT DOCUMENTS

| | | | |
|---|---|---|---|
| 3,097,646 | 7/1963 | Scislowicz | 128/214.4 |
| 3,233,727 | 2/1966 | Wilson | 215/247 |
| 3,853,127 | 12/1974 | Spademan | 128/214.4 |
| 3,923,065 | 12/1975 | Nozick et al. | 128/348 |
| 3,977,400 | 8/1976 | Moorehead | 128/214.4 |
| 4,149,535 | 4/1979 | Volder | 128/214.4 |
| 4,243,034 | 1/1981 | Brandt | 128/214.4 |

FOREIGN PATENT DOCUMENTS

| | | | |
|---|---|---|---|
| 141423 | 4/1920 | United Kingdom | 128/221 |
| 2019219 | 10/1979 | United Kingdom | 128/214 R |
| 2034185 | 6/1980 | United Kingdom | 128/214.4 |

Primary Examiner—Steven A. Bratlie
Attorney, Agent, or Firm—Robert S. Beiser; Alan R. Thiele

[57] ABSTRACT

An improved venipuncture device comprises a catheter having a catheter hub at one end with a needle having a needle hub at one end and a sharpened tip at the second end extending through the catheter and catheter hub. The needle is adapted for insertion and removal from the catheter. The improvement comprises a penetrable elastic sealing member sealed within the catheter hub. A compression mechanism compresses the sealing member in the same direction as the axis of the sealing member, thereby effectively resealing the opening through the sealing member created by withdrawal of the venipuncture needle.

3 Claims, 39 Drawing Figures

VENIPUNCTURE DEVICE

BACKGROUND OF THE INVENTION

The present invention relates generally to venipuncture devices and more particularly to an easily separable over-the-needle catheter insertion device.

Catheter insertion devices generally are widely available in the prior art. However, the hospital products industry continuously strives to improve such devices in an attempt to provide simpler, easier to use, disposable devices than are presently on the market. Several specific areas of endeavor have been pursued, such as maintaining the seal of the catheter upon removal of the insertion needle. Along these same lines an additional problem has been in providing an easily operable means of connecting the catheter hub to the needle hub so as to immovably join the two during insertion, but allow quick release when desired.

Numerous devices have been developed in order to overcome these problems, as best seen in the following U.S. patents:
U.S. Pat. No. 3,714,945—"Digit Manipulable Quick-Release Cannula Insertion Means"—F. S. Vayden—issued Feb. 6, 1973;
U.S. Pat. No. 3,097,646—"Venous Catheter Apparatus"—H. M. Scislowicz—issued July 16, 1963;
U.S. Pat. No. 3,245,698—"Latching Means"—C. T. Fromknecht—issued Apr. 12, 1966;
U.S. Pat. No. 3,394,954—"Tube Coupling for Medical Appliances"—R. N. Sarns—issued July 30, 1968;
U.S. Pat. No. 3,602,009—"Snap-On Ferrule"—P. Powell—issued Aug. 31, 1971;
U.S. Pat. No. 3,875,938—"Multi-Mode Cannulating Apparatus"—E. Mellor—issued Apr. 8, 1975;
U.S. Pat. No. 3,977,400—"Catheter Placement Unit with Resilient Sleeve and Manual Sleeve Closure"—H. R. Moorehead"—issued Aug. 31, 1976;
U.S. Pat. No. 3,853,127—"Elastic Sealing Member"—R. G. Spademan—issued Dec. 10, 1974;
U.S. Pat. No. 4,079,738—"Needle Restraining Apparatus"—K. Dunn, et al.—issued Mar. 21, 1978; and
U.S. Pat. No. 4,137,916—"Catheter Plug Assembly"—D. M. Killman, et al.—issued Feb. 6, 1979.

The above-listed devices have met with varying degrees of success. Accordingly it is an advantage of the present invention to provide an improved venipuncture device which contains a mechanism for maintaining the seal of the catheter assembly upon removal of the needle. It is an additional advantage of the invention to provide such a device which is low in cost and simple to manufacture. It is a further advantage of the invention to provide improved venipuncture devices which lock the catheter and needle hub assemblies during needle insertion, but which are easily releasable when desired.

SUMMARY OF THE INVENTION

The present invention is an improved venipuncture device comprising a catheter having a catheter hub attached at one end, and a needle having a needle hub attached at one end, and a sharpened tip at its second end. The needle extends coaxially through the catheter and has its sharpened tip extending from the catheter. The catheter hub is adapted for insertion and removal of the needle. The improvement comprises a penetrable elastic sealing member sealed within the catheter hub. A compression mechanism is utilized for compressing the sealing member in the same direction as its longitudinal axis. As a result the sealing member effectively reseals the opening created by withdrawal of the needle. The compression mechanism also has an aperture through it for passage of the needle. A retainer oppositely disposed to the compression mechanism supports the sealing member under compression and also allows passage of the needle.

In a preferred embodiment the compression mechanism comprises one or more springs coaxially aligned with the sealing member. The compression mechanism also includes a number of washers interposed between the springs and the sealing member that allows the compressive force of the springs to be uniformly distributed across the ends of the sealing member. At the same time the washers also allow the passage of the needle through the sealing member.

In an additional embodiment of the invention a number of incremental stops are provided within the catheter hub. A mechanism is provided for progressively compressing the sealing member. Thus, when the needle is fully withdrawn, the sealing member may be tightly compressed, thereby hermetically sealing the aperture created by the withdrawal of the needle.

In one embodiment of the invention the venipuncture device also includes a latching mechanism between the needle hub and the catheter hub which prevents movement or rotation of the needle in relation to the catheter during venipuncture. At the same time the latching mechanism is designed for quick and easy release of the needle hub from the catheter hub. This is particularly helpful during the venipuncture procedure in that following initial insertion of the catheter into the vein, the needle can be withdrawn into the catheter, thereby facilitating further insertion of the catheter into the vein. The latching mechanism comprises a loop member connected to the rear of the needle hub and having a prong attached at the other end of the loop adapted for releasable engagement with the catheter hub. The loop is constructed of a resilient material and is preferably formed as a curve between the front and back. This curve forcibly retains the prong against the catheter hub. A series of shoulders is integrally formed in the catheter hub so as to present a slot for engagement with the prong.

In a preferred embodiment the latch loop also includes a digit manipulable (finger grip) release, preferably in the form of a trigger or hook extending from the latch loop which may be used for disengaging the prong member from the catheter hub. This digit manipulable release is shaped to facilitate release and separation of the needle hub from the catheter hub whereby the sharpened needle tip may be withdrawn into the catheter.

In an additional embodiment of the invention the needle hub also includes a number of tabs extending at right angles, adapted for digit engagement so as to separate the needle hub from the catheter hub and thereby to withdraw the sharpened tip of the needle inside the catheter.

In a preferred embodiment the venipuncture device includes a pair of flexible wings, such as those described in U.S. Pat. No. 3,064,648, assigned to the assignee of the present invention, attached to the catheter hub which facilitates gripping of the device during venipuncture. The flexible wings also facilitate separation of the needle hub from the catheter hub, either by gripping the wings with one hand and the needle hub with a second hand and then separating the needle hub from the catheter hub, or by gripping the wings with the thumb and index finger and then pressing against the latch loop, or a tab on the needle hub with one of the other fingers. The wings are reduced in thickness along the catheter hub in order to make them flexible enough to easily raise vertically and pinch together for gripping.

In an alternative embodiment of the invention the latching mechanism comprises a hinged connector pivotably attached to the needle hub. A prong extends from one end of the hinged connector and is adapted for releasable engagement with the catheter hub. A slot may be integrally formed on the catheter hub for reception and abutment with the prong member. A digit manipulable (finger grip) release mechanism, preferably in a curved configuration, extends upwardly from the hinged connector in order to facilitate disengagement of the prong member from the catheter hub thereby releasing the catheter hub from the needle hub. The digit manipulable release mechanism also is adapted in shape and positioning for separating the needle hub from the catheter hub so as to move the needle outwardly from the catheter hub and thereby withdraw the needle tip inside of the catheter.

Similarly, the previously mentioned hinged connector may be pivotably attached to the catheter hub rather than the needle hub. The hinged connector includes a hinge centrally mounted on the flexible connector for facilitating pivotal movement of the flexible connector.

In an alternative embodiment of the invention, the latching mechanism comprises a bridge structure extending between the needle hub and the catheter hub and releasably attached to both. In addition to joining the needle hub with the catheter hub, the bridge also fixes the position of each respectively. The bridge mechanism also includes digit engageable means for release and separation of the catheter hub from the needle hub. In a preferred embodiment the bridge mechanism comprises a plurality of C-shaped prong members extending from first and second ends of the bridge and is adapted in size and position for reception on and attachment to corresponding reception slots integrally formed in the catheter hub and in the needle hub. As a result the catheter hub and the needle hub may be selectively attached and fixedly positioned in relation to each other, or released from each other as desired.

In an additional embodiment of the invention a locking mechanism is integrally formed within the catheter hub or the needle hub for joining the two together. The locking mechanism comprises a lug integrally formed and extending from the needle hub. A lug slot is integrally formed within the catheter hub for telescopic reception of the lug member. A rotation cavity is integrally formed within the catheter hub so that when the needle hub is inserted into the catheter hub, the lug slides through the lug slot until it reaches the rotation cavity. At that time the lug and the needle hub are rotated, thereby locking the two together. Correspondingly, the hubs may be separated by rotating the needle hub until the lug is aligned with the lug slot. The needle hub may then be withdrawn from the catheter hub. The previously mentioned locking mechanism may alternatively comprise a lug extending from the catheter hub in a lug slot integrally formed within the needle hub. In addition the lug slot may be spiraled, eliminating the need for the rotation cavity. Alternatively, the rotation cavity may include a stop formed therein for limiting rotation of the lug, or may include a movable tab, displaceable by the lug during rotation which locks in place behind the lug, preventing further rotation.

In an alternative embodiment of the invention the catheter hub and the needle hub are rectangular in shape and adapted for snugly fitting telescopic engagement. The rectangular shape and snug fit prevents rotation or movement of the needle in relation to the catheter.

In an additional embodiment the catheter may include a sidewardly angled duct extending from the catheter hub and defining a side port for conducting fluid to the device (a Y catheter). In one type of locking mechanism, a tubular connector either integrally formed or attached to the needle hub extends from the needle hub and is adapted for snugly fitting telescopic reception of the proximal portion of the catheter hub. The tubular connector has a duct slot integrally formed therein and is adapted for slidable engagement with the duct member. Thus, the needle hub and the catheter hub may be selectively joined and fixedly positioned in relation to each other, thereby preventing movement of the needle within the catheter during venipuncture.

In a preferred embodiment of the invention the venipuncture device further includes a removable needle sheath attached to either the catheter hub or needle hub and extending over the needle. A needle sheath port is integrally formed at the proximal end of the needle hub and is adapted for telescopic reception of the needle sheath member. The needle sheath thereby acts as a gripping extension from the device, facilitating insertion of the needle during venipuncture. In a preferred embodiment the previously mentioned flexible wings are pinched between the thumb and the index finger of the user and the palm of the user's hand rests against the proximal end of the needle sheath positioned within the needle sheath port. As a result the device may be gripped in a manner particularly suitable for ease of venipuncture.

DETAILED DESCRIPTION OF THE PREFERRED EMBODIMENT

While this invention is susceptible of embodiment in many different forms there is shown in the drawings and will herein be described in detail, several specific embodiments, with the understanding that the embodiments illustrated are an exemplification of the principles of the invention and not intended to limit the invention to the embodiments illustrated.

Figures 1, 2, 3, 4, 4A, 4B, 4C, 4D, 4E:
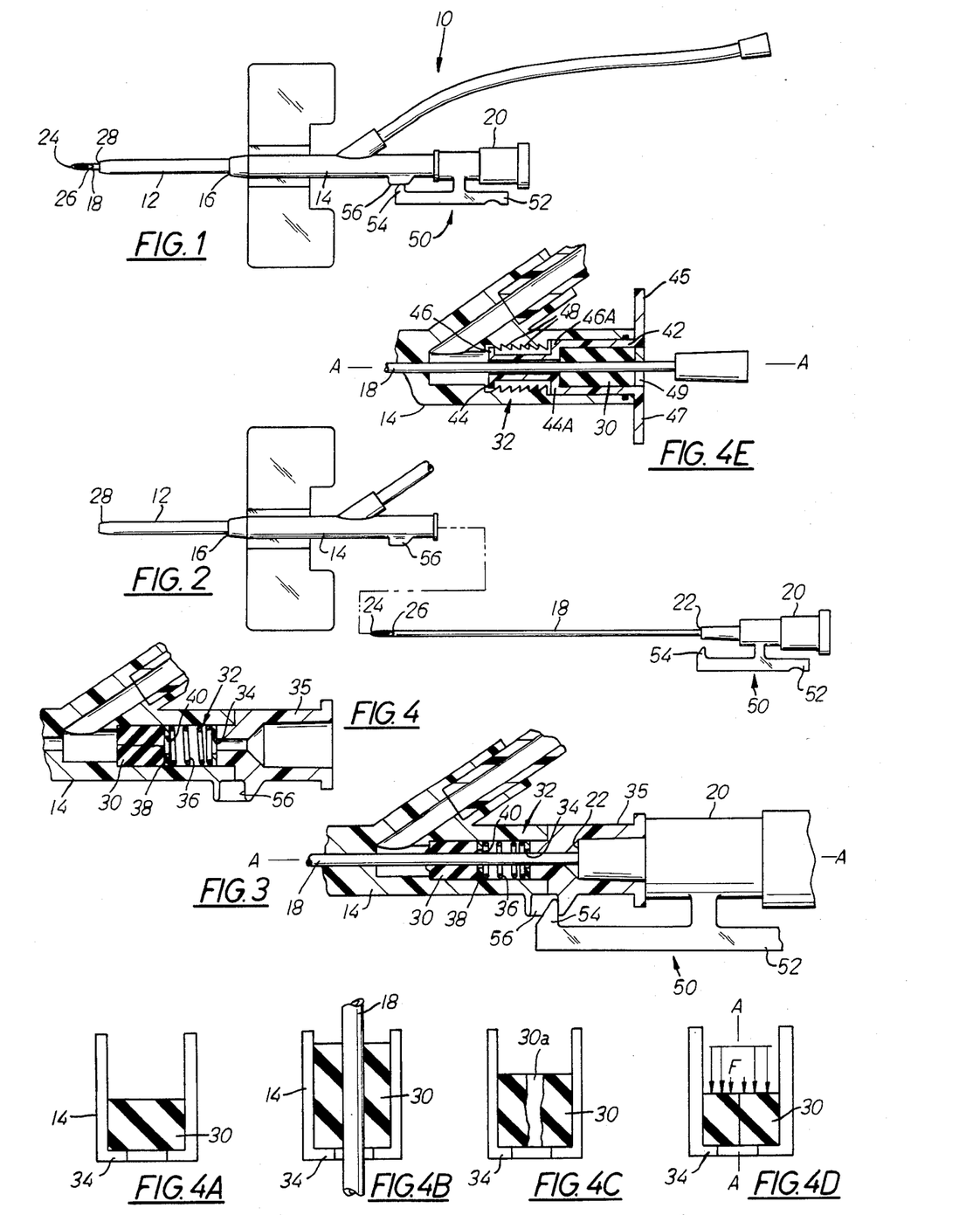
FIG. 1 of the drawings is a top view of an improved venipuncture device.
FIG. 2 of the drawings is a top view, partially broken away of the improved venipuncture device of FIG. 1 showing in particular a needle and needle hub removed from a catheter and catheter hub.
FIG. 3 of the drawings is a partial side cutaway view of the improved venipuncture device of FIG. 1 showing in particular a needle extending through a penetrable elastic sealing member positioned within the catheter hub.
FIG. 4 of the drawings is a partial side cutaway view of the improved venipuncture device of FIG. 3 showing in particular the penetrable elastic sealing member in a sealed configuration upon removal of the needle and needle hub shown in FIGS. 2 and 3.
FIG. 4A of the drawings is a partial side cut away view of the improved venipuncture device of FIG. 1 showing in particular a penetrable elastic sealing member positioned within the catheter hub.
FIG. 4B of the drawings is a partial side cut away view of the improved venipuncture device of FIG. 2 showing in particular a needle extending through the penetrable elastic sealing member.
FIG. 4C of the drawings is a partial side cut away view of the improved venipuncture device of FIG. 4B showing in particular a pathway remaining in the penetrable elastic sealing member upon removal of the needle.
FIG. 4D of the drawings is a partial side cut away view of the improved venipuncture device of FIG. 4C showing in particular force being applied along axis A—A so as to compress and seal the penetrable elastic sealing member.
FIG. 4E of the drawings is a partial side cut away view of the improved venipuncture device showing in particular a slide mechanism for incrementally compressing the penetrable elastic sealing member.

As best seen in FIGS. 1 and 2 of the drawings, in a preferred embodiment, improved venipuncture device 10 comprises a catheter 12 having a catheter hub 14 attached thereto at proximal end 16 of catheter 12. Needle 18 having needle hub 20 attached at proximal end 22 and sharpened tip 24 at distal end 26 extends coaxially through catheter 12 with sharpened tip 24 extending from catheter 12 at its distal end 28. The outside diameter of needle 18 is slightly less than the inside diameter of catheter 12 thereby allowing insertion and removal of needle 18 from catheter 12.

As best seen in FIGS. 3 and 4 of the drawings, improved venipuncture device 10 includes a penetrable elastic sealing member 30 positioned within catheter hub 14 and which is of a size and material adapted for sealing catheter hub 14. Compression mechanism 32 compresses penetrable elastic sealing member 30 in the direction of its longitudinal axis A—A so as to maintain the seal of catheter hub 14 upon withdrawal of needle 18 from the sealing member 30. In addition compression mechanism 32 has an aperture 34 which allows the passage of needle 18 into and through sealing member 30.

In a preferred embodiment compression mechanism 32 comprises one or more springs such as spring 36 shown in FIGS. 3 and 4 which are aligned along the axis A—A and juxtaposed to sealing member 30 so as to compress it within catheter hub 14. In addition, in a preferred embodiment compression mechanism 32 also includes one or more washers such as washer 38 which circumscribes axis A—A, and is juxtaposed between spring 36 and sealing member 30 so as to distribute the compressive force of spring 36 across the end of sealing member 30 thereby compressing sealing member 30 uniformly. At the same time washer 38 has an aperture 40 which allows the passage of needle 18 through it and thereby through sealing member 30 and catheter 12. Spring 36 is held in place by portion 35 of catheter hub 14, which is joined thereto using conventional techniques such as ultrasonic or solvent sealing.

As best seen in FIGS. 4A through 4D, prior to penetration by needle 18, penetrable sealing member 30 hermetically seals catheter hub 14. Sealing member 30 is a unitary mass of elastomeric material. As seen in FIG. 4B needle 18 is inserted through aperture 34 and through sealing member 30. Being resilient, sealing member 30 hermetically seals itself about needle 18. As seen in FIG. 4C, upon withdrawal of needle 18, a channel or pathway 30a remains through sealing member 30. In medical applications requiring sterility (such as a catheter device) the presence of an open channel allows contamination of the interior of the device, and leakage of I.V. solution, making it unsuitable for such use. Therefore it is essential that sealing member 30 be hermetically sealed. As best seen in FIG. 4D, in order to accomplish such sealing, a force (designated F) is applied along axis A—A so as to compress sealing member 30 thereby closing channel 30a.

In a preferred embodiment compression mechanism 30 utilizes spring 36 to hermetically seal catheter hub 14 upon removal of needle 18. However, in an alternative embodiment of the invention, as best seen in FIG. 4E of the drawings the compression mechanism 32 may simply comprise a mechanical means for compressing penetrable sealing member 30 along axis A—A after withdrawal of needle. For example, slide 42 having flanges 44 and 46 extending therefrom may be drawn toward needle hub 20 thereby compressing sealing member 30. Incremental stops 48 are used to retain flanges 44 and 46 and thereby to retain penetrable sealing member 30 in a compressed configuration. Grips 45 and 47 are used to pull slide 42 backward. This causes slide 42 to compress sealing member 30 between shoulders 44A and 46A and retaining member 49, integrally formed at the proximal end of catheter hub 14.

Returning to FIG. 1 of the drawings, in a preferred embodiment venipuncture device 10 includes a latching mechanism 50 interconnecting needle hub 20 with catheter hub 14. Latching mechanism 50 prevents movement or rotation of needle 18 within catheter 12 during venipuncture. At the same time latching mechanism 50 allows quick release of needle hub 20 from catheter hub 14 so as to allow withdrawal of needle 18 from catheter 12 as desired. As shown in FIGS. 1 and 2, latching mechanism 50 comprises a pivotable arm 52 attached to needle hub 20 having a prong 54 extending into and adapted for removable engagement with a corresponding slot 56 integrally formed in catheter hub 14.

Figures 5, 6, 7, 8:
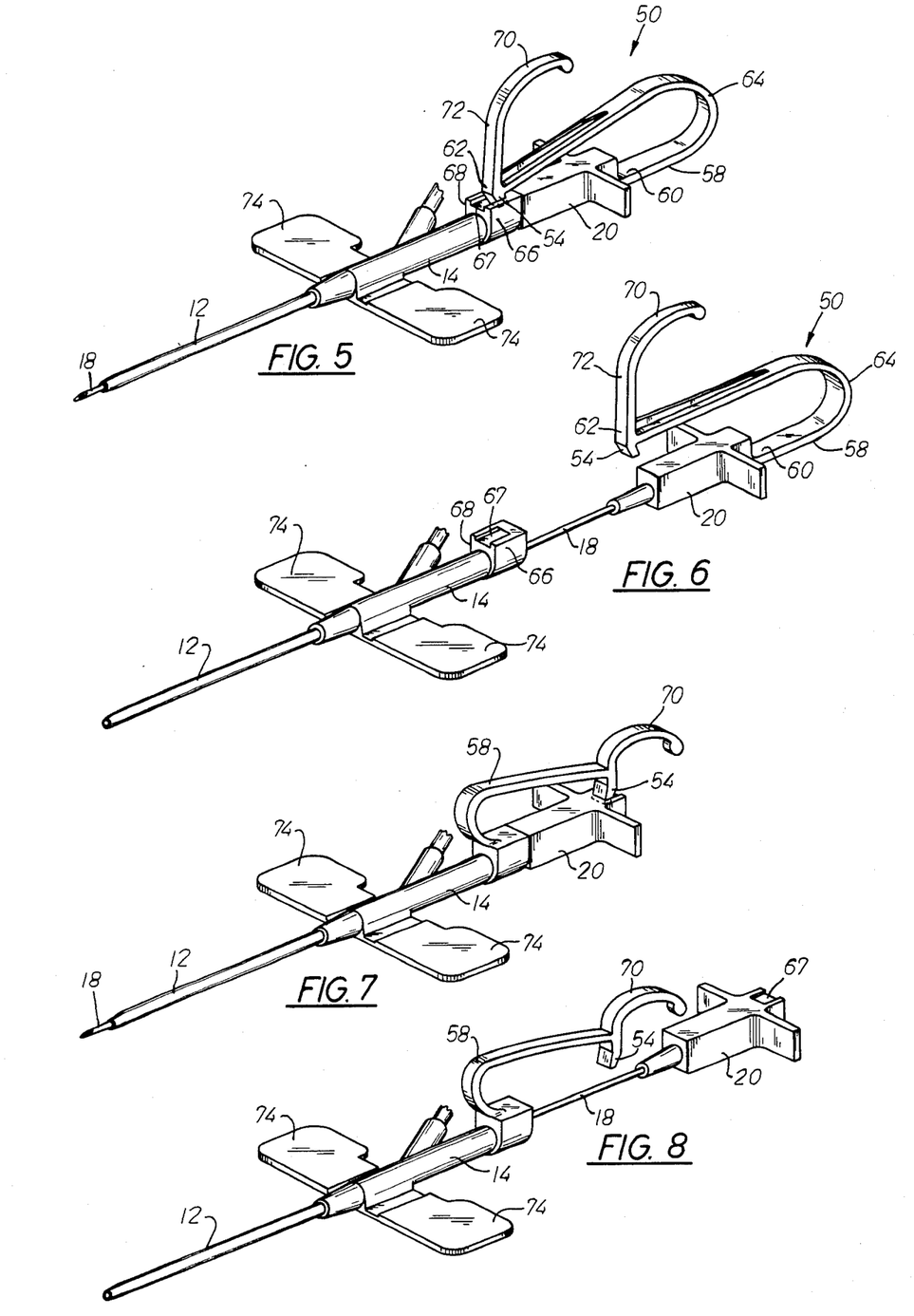
FIG. 5 of the drawings is a side perspective view of an improved venipuncture device showing in particular a latch loop mechanism for locking the needle hub to the catheter hub.
FIG. 6 of the drawings is a side perspective view of the improved venipuncture device of FIG. 5 showing in particular the needle hub and latch loop partially separated from the catheter hub.
FIG. 7 of the drawings is a side perspective view of an improved venipuncture device showing in particular a latch loop member extending from the catheter hub to the needle hub.
FIG. 8 of the drawings is a side perspective view of the improved venipuncture device of FIG. 7 showing in particular the catheter hub and latch loop partially separated from the needle hub.

As best seen in FIG. 5 of the drawings, in a preferred embodiment latching mechanism 50 comprises a latch loop member 58 connected at first end 60 to needle hub 20 and having a prong member 54 attached at a second end 62. Latch loop member 58 is adapted for releasable engagement with catheter hub 14 and is constructed of a resilient material. A distinguishing feature of latch member 58 over latches seen in the prior art is curved portion 64 between first end 60 and second end 62 which effectively forces prong 54 towards first end 60 of needle hub 20. In addition, curved portion 64 tends to urge prong 54 to snap into undercut 67 between shoulders 66 and 68 (integrally formed in catheter hub 14 or extending therefrom). Thus, catheter 12 and needle 18 may be inserted into the vein of the patient with needle 18 maintained in position within catheter 12. Following initial insertion, prong 54 may be raised out of the space between shoulders 66 and 68 so as to disengage needle hub 20 from catheter hub 14. Also, when prong 54 is lifted, curved portion 64 pulls prong 54 away from undercut 67, to prevent re-engagement of prong 54. Needle 18 may then be withdrawn within catheter 12 facilitating further catheterization.

An additional feature of latch loop 58 is digit manipuable release arm 70 extending from prong member 54. The curved configuration of release arm 70 allows single digit release of prong 54 from catheter hub 14. In addition, portion 72 of release arm 70 extends perpendicularly from prong 54. As a result, portion 70 may be pushed away from catheter 12 thereby separating needle hub 20 from catheter hub 14 as best seen in FIG. 6 of the drawings.

In an alternative embodiment of the invention as seen in FIGS. 7 and 8 of the drawings, latch loop member 58 may extend from catheter hub 14 with prong member 54 positioned for releasable engagement with needle hub 20. Digit manipulable release arm 70, in this embodiment extends rearwardly from loop 58 so as to allow single digit release of needle 20 from catheter hub 14.

In this and other preferred embodiments a pair of flexible wings 74 extend from catheter hub 14. The wings are positioned so that when folded and raised vertically they may be pinched together thereby gripping venipuncture device 10. This position facilitates insertion of needle 18 and catheter 12 into a patient's vein. In addition, in the embodiments shown in FIGS. 5 through 8 as well as several embodiments catheter hub 14 may be separated from needle hub 20 using a single hand to both grip flexible wings 74 and release arm 70.

Figure 9:
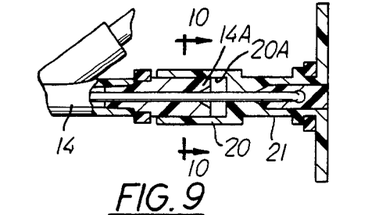
FIG. 9 of the drawings is a partial side cut away view of an improved venipuncture device showing in particular a rectangular catheter hub and a rectangular needle hub adapted for telescopic reception of the catheter hub in order to prevent rotation and movement of the needle within the catheter and catheter hub.
Figure 10:
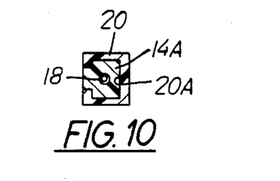
FIG. 10 of the drawings is a cut away view of the improved venipuncture device of FIG. 9 taken along axis 10—10 showing in particular the rectangular configuration of the needle hub and catheter hub.

As best seen in FIGS. 9 and 10 of the drawings catheter hub 14 may include a rectangular appendage 14a at its proximal end adapted for telescopic insertion into a corresponding chamber 20a at the distal end of needle hub 20. As a result of the rectangular configuration of appendage 14a needle 18 is fixedly positioned within catheter 12 and may not be rotated.

Figure 11:
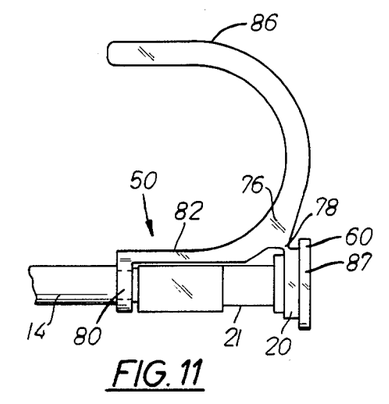
FIG. 11 of the drawings is a partial side view of an improved venipuncture device showing in particular a pivotable connecting mechanism.
Figure 12:
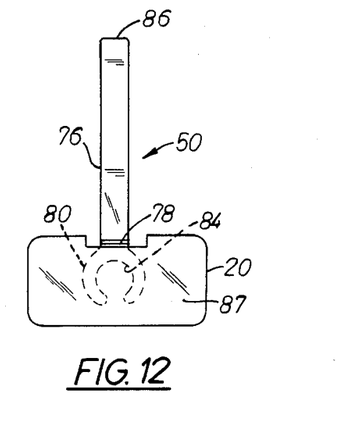
FIG. 12 of the drawings is a rear view of the improved venipuncture device of FIG. 11.

As best seen in FIGS. 11 and 12 of the drawings in an alternative embodiment of the invention latching mechanism 50 may comprise a hinged connector 76 pivotably attached to needle hub 20. By pivotably attached it is meant that the connector may be attached by a hinge such as living hinge 78 and extend towards the proximal portion of catheter hub 14. The term "living hinge" is meant to describe a resilient piece of plastic which may be flexed repeatedly without tearing or fracturing. Alternatively, pivot 78 may comprise a simple mechanical hinge. In any event, as shown hinged connector 76 includes a circular prong 80 extending from bridge 82. Prong 80 is adapted for releasable engagement about catheter hub 14. By this it is meant that the inside diameter 84 of prong 80 is slightly larger than the outside diameter of catheter hub 14. At the same time, hinged connector 76 is of a rigid material so as to allow resilient prong 80 to snap-fit over catheter hub 14. In order to release hinged connector 76 a digit manipulable release arm 86 extends upwardly from flexible hinge 78 and is in a curved configuration so as to allow a single digit to snap prong member 80 off of catheter hub 14. Release arm 86 is also shaped so that needle hub 20 may be moved rearwardly from catheter hub 14 in order to withdraw needle 18 into catheter 12. Push off tab 87 is also provided at the proximal end 60 of needle hub 20 in order to pull needle hub 20 away from catheter hub 14.

Figures 13, 14:
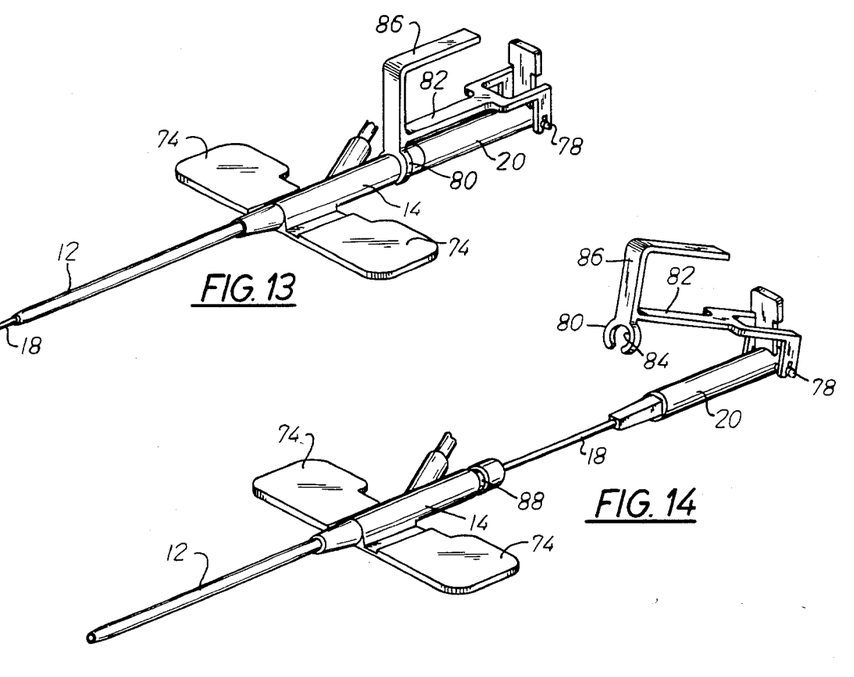
FIG. 13 of the drawings is a side perspective view partially broken away of an improved venipuncture device showing in particular a pivotable locking mechanism.
FIG. 14 of the drawings is a side perspective view partially broken away of the improved venipuncture device of FIG. 13 showing in particular the pivotable locking mechanism and the needle hub partially separated from the catheter and catheter hub.

As seen in FIGS. 13 and 14 of the drawings release arm 86 may take a right angle configuration and may extend upwardly from prong 80 rather than from hinge 78. As further seen in FIGS. 13 and 14 hinge 78 may be a simple mechanical hinge. Catheter hub 14 may also include a circular groove 88 circumferentially positioned about its proximal portion and adapted for reception and rotation of prong 80. In this embodiment the inside diameter 84 of prong 80 is slightly larger than the outside diameter of groove 88. In an additional alternative of the invention (not shown) bridge 82 may simply have two circular prong members such as circular prong 80 extending from each end and adapted for releasable engagement with grooves such as groove 88 shown in FIG. 14. Release arm 86 or other commonly known appendages may be used for removing bridge 82 from device 10.

Figures 15, 16:
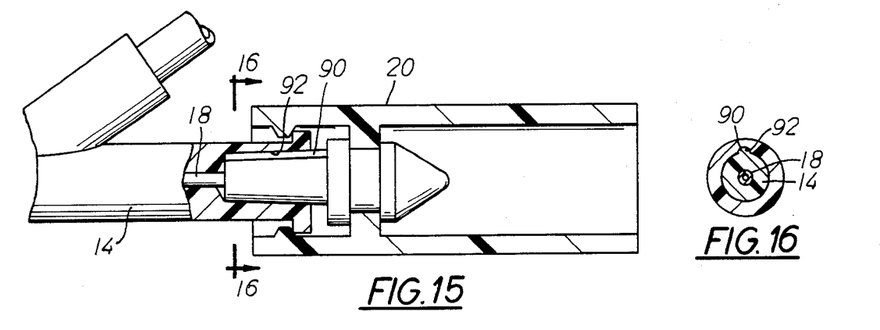
FIG. 15 of the drawings is a partial side cut away view of an improved venipuncture device showing in particular a lug locking mechanism for fixedly attaching a needle hub to a catheter hub.
FIG. 16 of the drawings is a cut away view taken along axis 16—16 of the improved venipuncture device of FIG. 15.
Figures 17, 18:
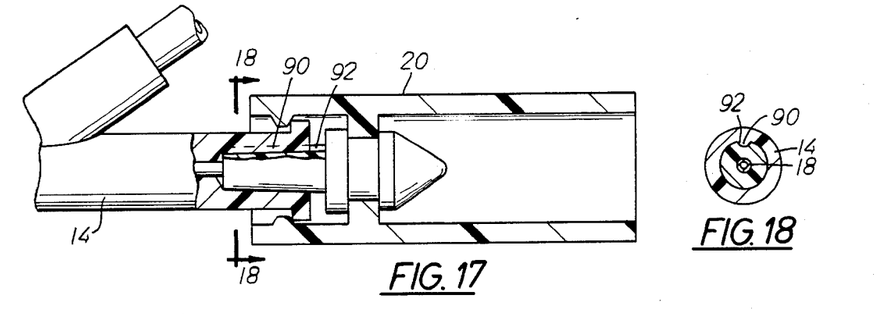
FIG. 17 of the drawings is a partial side cut away view of an improved venipuncture device showing in particular a lug locking mechanism in which the lug extends from the catheter hub.
FIG. 18 of the drawings is a cut away view taken along section 18—18 of the improved venipuncture device of FIG. 17.

An additional feature of the invention is the use of a locking mechanism for fixing the position of needle 18 within catheter 12, while at the same time allowing release of needle 18 from catheter 12 when required. This may be accomplished using a variety of methods. For example, as seen in FIGS. 15 and 16 a lug 90 is integrally formed and extends from catheter hub 14. A lug slot 92 is integrally formed in catheter hub 14 so that needle hub 20 and catheter hub 14 can be joined together and the position of needle 18 locked in place. Correspondingly, lug 90 may be formed in catheter hub 14 and lug slot 92 may be formed in an extension of needle hub 20, as seen in FIGS. 17 and 18.

Figures 19, 20:
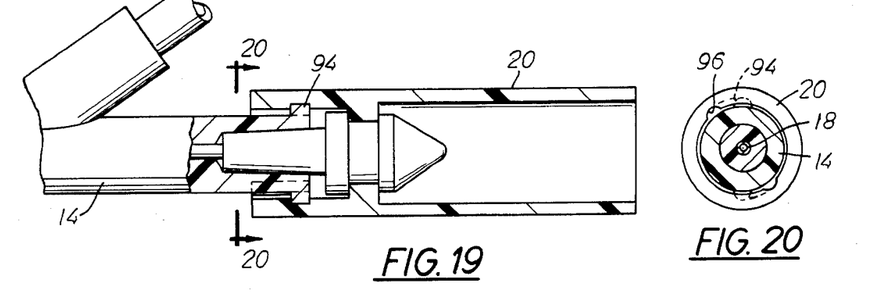
FIG. 19 of the drawings is an improved venipuncture device showing in particular a rotatable lug locking mechanism.
FIG. 20 of the drawings is a view in vertical section of an improved venipuncture device of FIG. 19 taken along axis 20—20.
Figures 21, 22:
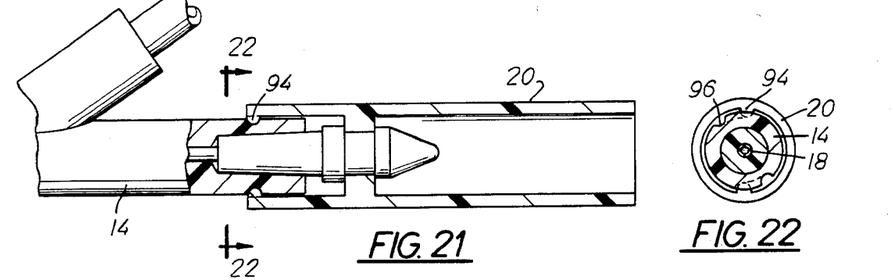
FIG. 21 of the drawings is a partial side cut away view of an improved venipuncture device showing in particular an alternative rotatable lug locking mechanism.
FIG. 22 of the drawings is a view in vertical section of the improved venipuncture device of FIG. 21 taken along line axis 22—22.
Figure 23:
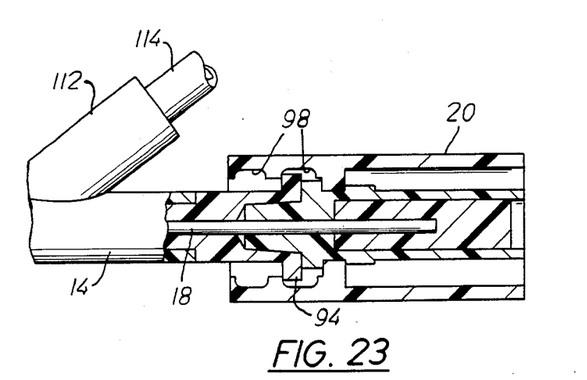
FIG. 23 of the drawings is a partial top cut away view of an improved venipuncture device showing in particular an incremental series of locking apertures adapted for locking a needle hub and catheter hub at a variety of positions in relation to each other.

Similar locking mechanism may be seen in FIGS. 19 through 22. In FIGS. 19 and 20, lug 94 is positioned for telescopic reception into lug slot 96. Alternatively, as seen in FIGS. 21 and 22, lug 94 may be formed in needle hub 20 and lug slot 96 may be formed in catheter hub 14. Again, lug 94 is telescopically received within lug slot 96 and needle hub 20 is rotated in relation to catheter hub 14 so as to cause the locking of each to the other. Alternatively, as best seen in FIG. 23 of the drawings, lug 94 may be inserted and rotated within needle hub 20 at a variety of depths so as to position needle 18 correspondingly at a variety of depths. For example, as seen in FIG. 23 a plurality of rotation chambers 98 may be used for positioning needle 18 in a variety of depths within catheter hub 14.

Figure 24:
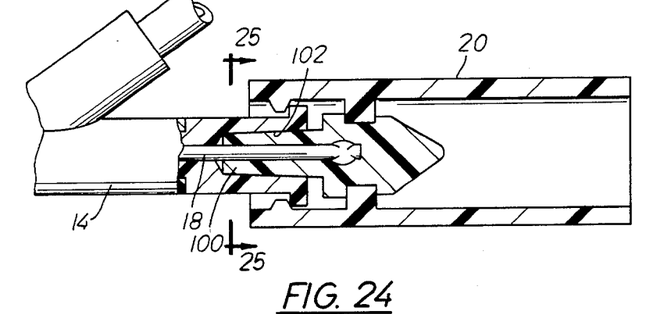
FIG. 24 of the drawings is a partial side cut away view of an improved venipuncture device showing in particular a D-locking apparatus.
Figure 25:
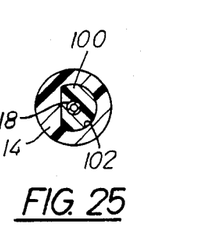
FIG. 25 of the drawings is a view in vertical section of the improved venipuncture device of FIG. 24 taken along lines 25—25.
Figure 26:
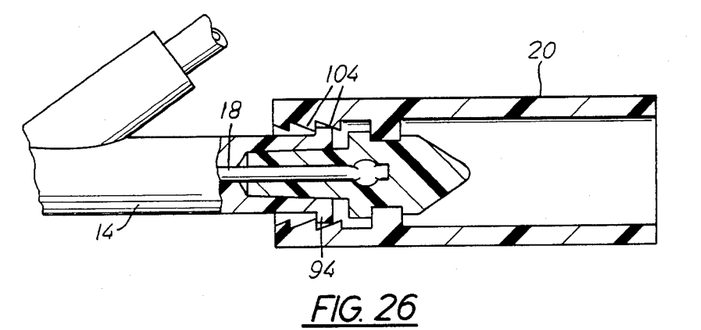
FIG. 26 of the drawings is a partial side cut away view of an improved venipuncture device showing in particular an incremental series of notches adapted for a variety of compressive settings of a penetrable sealing member.

In FIGS. 24 and 25 needle hub 20 has a D-shaped appendage 100 fixedly attached to and extending therefrom which holds needle 18. This D-shaped appendage is inserted into a corresponding aperture 102 within catheter hub 14. As a result the position of needle 18 is fixed. As further seen in FIG. 26 a series of notches 104 may be used for progressively fixing the depth of penetration of needle 18 within catheter 12 by abuting lug 94 against one of notches 104. Needle 18 may be removed by rotating needle hub 20 until lug 94 does not rest against one of notches 104 and then withdrawing it.

Figure 27:
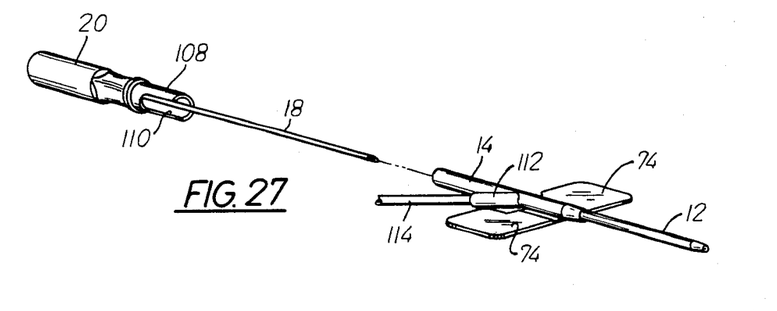
FIG. 27 of the drawings is a side perspective view partially broken away of an improved venipuncture device showing in particular a needle hub having a slot integrally formed therein adapted for telescopic reception of a side duct integrally formed on the catheter hub.
Figure 28:
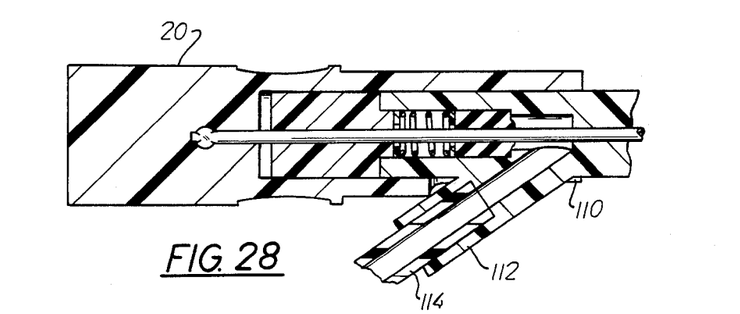
FIG. 28 of the drawings is a partial view in horizontal section of the improved venipuncture device of FIG. 27.

As best seen in FIGS. 27 and 28 of the drawings needle hub 20 may include a tubular appendage 108 having a slot 110 integrally formed therein. Tubular extension 108 is adapted for telescopic engagement with the proximal portion of catheter hub 14. In a preferred embodiment catheter hub 14 has a side duct 112 extending angularly therefrom and adapted for connection to a length of flexible tubing 114. Such flexible tubing allows the administration of medicaments into catheter 12 or removal of a desired quantity of blood taken from a patient's vein. Slot 110 is adapted for slidable fixation about side duct 112 so as to fix the position of needle hub 20 in relation to catheter hub 14.

Figure 29:
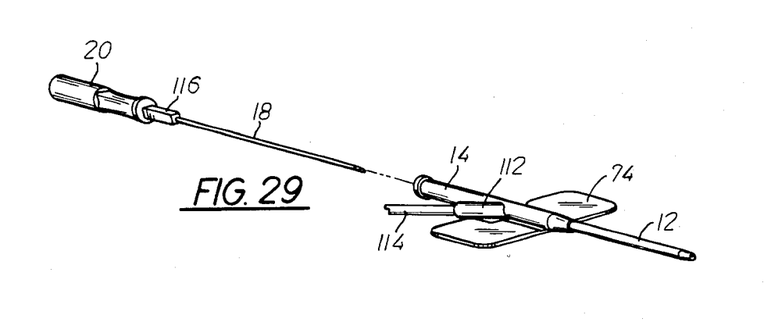
FIG. 29 of the drawings is a side perspective view partially broken away of an improved venipuncture device showing in particular a needle hub having a trapezoidal extension adapted for insertion into a corresponding aperture within a catheter hub, for fixedly maintaining the position of the needle within the catheter and catheter hub.
Figure 30:
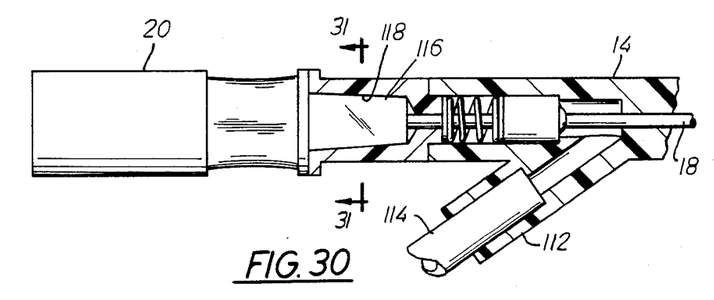
FIG. 30 of the drawings is a partial top cut away view of the improved venipuncture device of FIG. 29.
Figure 31:
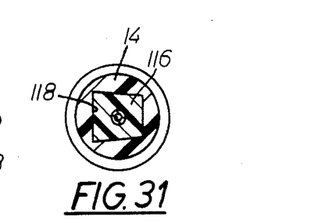
FIG. 31 of the drawings is a view in vertical section of the improved venipuncture device of FIG. 30 taken along lines 31—31.

As seen in FIGS. 29 through 31, in an alternative embodiment, needle hub 20 may also include a trapezoidal (or a rectangular) extension 116 in which needle 18 is coaxially mounted. A corresponding aperture 118 is formed within catheter hub 14 for the telescopic reception of extension 116. As a result, upon insertion of needle 18 and extension 116 into catheteter hub 14, trapezoidal extension 116 becomes fixedly mounted, thereby preventing movement or rotation of needle 18 within catheter 12.

It should be noted that although in a preferred embodiment venipuncture device 10 includes compression mechanism 32, alternative embodiments of the invention may include the previously mentioned latching or locking mechanisms without the use of such a compression mechanism for maintaining the seal of venipuncture device 10. In those embodiments a conventional rubber seal is used to seal venipuncture device 10.

It should be further noted that needle 12 can be "fixed" in three modes:
1. Rotational
2. Distal direction
3. Proximal direction.

Figure 32:
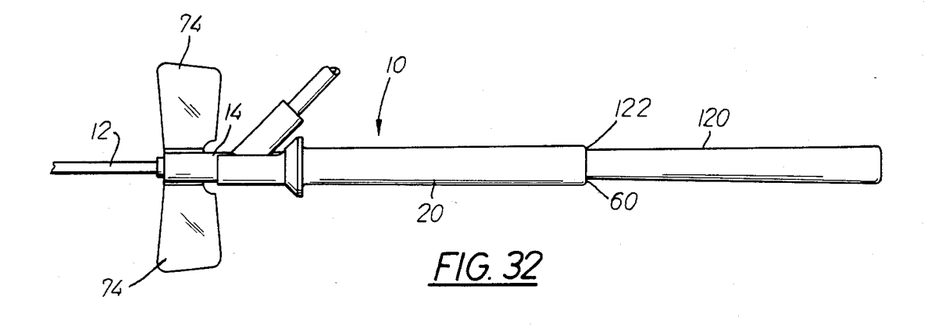
FIG. 32 of the drawings is a top view of an improved venipuncture device showing in particular a needle sheath used as a handle extension.

As best seen in FIG. 32 of the drawings improved venipuncture device 10 may include a flexible needle sheath 120 which is tubular for positioning over catheter 12 and needle 18 during shipment. Upon removal for use, flexible needle sheath 120 is insertable into a correspondingly shaped needle sheath port 122 at the proximal end 60 of needle hub 20. Flexible needle sheath 120 provides a longer gripping surface on needle hub 20 so as to facilitate catheter handling during insertion.

Figure 33:
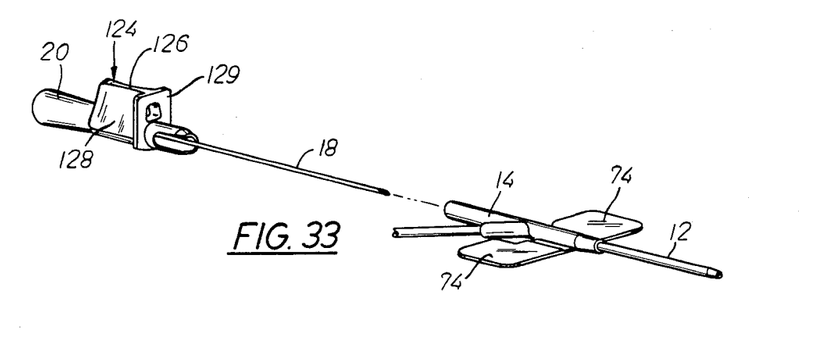
FIG. 33 of the drawings is a side perspective view, partially broken away of an improved venipuncture device showing in particular a needle hub having a tubular extension and a gripping portion extending therethrough.
Figure 34:
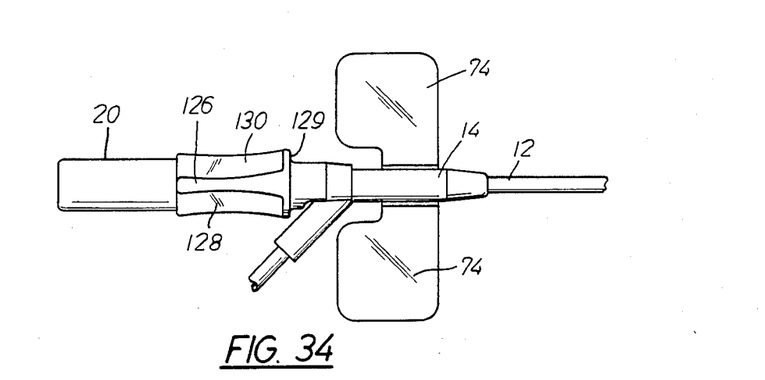
FIG. 34 of the drawings is a top view, partially broken away of the improved venipuncture device of FIG. 33.

As best seen in FIGS. 33 and 34 of the drawings, needle hub 20 may include a gripping portion 124 particularly adapted for gripping device 10 during venipuncture. As shown, gripping portion 124 includes rib 126 having curved faces 128 and 130 adapted for pinching between the thumb and index finger of the user. Front plate 129 is normally disposed from needle hub 20 and positioned in front of rib 126 for pushing against when performing venipuncture. As a result, device 10 is particularly easy to handle and use. In addition, plate 129 may be pushed rearwardly following venipuncture in order to separate needle hub 20 from catheter hub 14, or may be gripped by a second hand for effecting such separation.

It should be noted that catheter hub 14, and needle hub 20, as shown in FIGS. 1-4 are preferably constructed of a substantially rigid plastic material such as PVC, polycarbonate, acrylonitrile butadiene styrene or other commonly known moldable plastic.

The foregoing description and drawings merely explain and illustrate the invention, and the invention is not limited thereto, except insofar as the appended claims are so limited, as those skilled in the art who have the disclosure before them will be able to make modifications and variations therein without departing from the scope of the invention.

We claim:

1. An improved venipuncture device comprising catheter means having a catheter hub attached thereto at a first end;

needle means having needle hub means attached thereto at a first end and a sharpened tip at a second end, said needle means extending coaxially through said catheter means with said sharpened tip extending from said catheter means at a second end and being adapted for insertion and removal from said catheter means;

a penetrable elastic sealing member positioned within and adapted for sealing said catheter hub;

compression means for the compression of said penetrable elastic sealing member coincident with the longitudinal axis of said penetrable elastic sealing member, said compression means having an aperture therethrough for the passage of said needle means;

said compression means being constructed and arranged to reseal the opening through said penetrable elastic sealing member created by the withdrawal of said needle means from said penetrable elastic sealing member;

said compression means comprising; a plurality of spring members coaxially aligned and juxtaposed to said penetrable elastic sealing member for the compression of said penetrable elastic sealing member.

2. The invention according to claim 1 in which said compression means further comprises:

a plurality of washer members, each washer member being coaxially aligned and juxtaposed between said penetrable elastic sealing member and one of said spring members so as to distribute the compressive force of said spring member across the end of said penetrable elastic sealing member thereby compressing it uniformly, while at the same time allowing passage of said needle means therethrough.

3. The invention according to claim 1 in which said compression means further includes:

incremental stop means for the progressive application of compression upon said penetrable elastic sealing member upon withdrawal of said needle means from said sealing member.

* * * * *